(12) United States Patent
Corbo et al.

(10) Patent No.: US 8,613,911 B2
(45) Date of Patent: Dec. 24, 2013

(54) COMPOSITIONS HAVING A PLURALITY OF DISCRETE EMULSIONS

(75) Inventors: Faith A. Corbo, Roxbury, CT (US); Qi Hong, Whippany, NJ (US); Anthony D. Gonzalez, Oak Ridge, NJ (US)

(73) Assignee: Avon Products, Inc, New York, NY (US)

( * ) Notice: Subject to any disclaimer, the term of this patent is extended or adjusted under 35 U.S.C. 154(b) by 0 days.

(21) Appl. No.: 13/129,184

(22) PCT Filed: Nov. 18, 2009

(86) PCT No.: PCT/US2009/064885
§ 371 (c)(1),
(2), (4) Date: May 13, 2011

(87) PCT Pub. No.: WO2010/065297
PCT Pub. Date: Jun. 10, 2010

(65) Prior Publication Data
US 2011/0223120 A1    Sep. 15, 2011

Related U.S. Application Data

(60) Provisional application No. 61/119,532, filed on Dec. 3, 2008.

(51) Int. Cl.
*A61K 9/107* (2006.01)
*A61K 8/66* (2006.01)
*A61Q 1/02* (2006.01)
*A61Q 17/04* (2006.01)

(52) U.S. Cl.
USPC ............... 424/63; 424/59; 514/770; 514/937

(58) Field of Classification Search
None
See application file for complete search history.

(56) References Cited

U.S. PATENT DOCUMENTS

| 4,184,978 | A | | 1/1980 | France et al. |
| 5,380,520 | A | * | 1/1995 | Dobbs .............................. 424/61 |
| 5,851,541 | A | * | 12/1998 | Corey et al. .................... 424/401 |
| 5,912,002 | A | | 6/1999 | Grieveson et al. |
| 5,935,589 | A | * | 8/1999 | Mukherjee et al. ........... 424/401 |
| 6,245,344 | B1 | * | 6/2001 | Thibant et al. ................ 424/401 |
| 6,503,891 | B1 | * | 1/2003 | Marquis et al. .................. 514/95 |
| 6,516,838 | B2 | * | 2/2003 | Thibant et al. ................ 141/100 |
| 6,844,009 | B1 | | 1/2005 | Degert et al. |
| 7,078,025 | B2 | * | 7/2006 | Kripp et al. ................... 424/70.2 |
| 2005/0002976 | A1 | * | 1/2005 | Wu ................................. 424/401 |
| 2006/0128883 | A1 | * | 6/2006 | Garrison et al. ............... 524/588 |

FOREIGN PATENT DOCUMENTS

WO    WO 9504517        *   2/1995
WO    WO 9504517 A1   *   2/1995

* cited by examiner

*Primary Examiner* — Daniel Sullivan
*Assistant Examiner* — Dominic Lazaro
(74) *Attorney, Agent, or Firm* — David M. Joyal; Jean M. McGillycuddy; Brian C. Remy

(57) ABSTRACT

A cosmetic composition comprising a first emulsion and a second emulsion and optionally one or more additional emulsions, each of the two or more emulsions being discretely contained within the composition and comprising an inner phase and an outer phase, each of the two or more emulsions being independently a water-in-oil emulsion, an oil-in-water emulsion, an oil-in-oil emulsion, a polyol-in-oil emulsion, a water-in-silicone emulsion, a silicone-in-water emulsion, or a polyol-in-silicone emulsion in physical contact with at least one other emulsion, at least one of the two or more emulsions being visually distinct from the others, and each of the two or more emulsions as well as the composition being independently both physically and visually stable within the composition for at least six months at ambient temperature.

22 Claims, No Drawings

US 8,613,911 B2

COMPOSITIONS HAVING A PLURALITY OF DISCRETE EMULSIONS

RELATED APPLICATIONS

This application claims priority to International Application Ser. No. PCT/US09/64885 filed Nov. 18, 2009, which claims priority U.S. Provisional Patent Application Ser. No. 61/119,532, filed Dec. 3, 2008, the contents of which are hereby incorporated by reference in their entirety.

FIELD

This disclosure relates generally to emulsion compositions, and more specifically to compositions having two or more distinct emulsions.

BACKGROUND

Cosmetic and toiletry products comprising a gel phase and a second emulsion phase have been disclosed in U.S. Pat. No. 4,335,103 to Barker et al. and in U.S. Pat. No. 6,213,166 to Thibiant et al. Such products are useful for numerous reasons, including but not limited to the visual effect produced.

Such gel-based products known in the art generally tend not to be stable, that is, they do not maintain their visual appearance when subjected to alternating freezing/thawing conditions or to variations in temperature. Furthermore, such gel-based products generally cannot include two incompatible active ingredients in the same composition.

In accordance with teachings in the art, one of ordinary skill would expect that a multiple-phase product where the two phases are emulsions with similar continuous and discontinuous phases would not be stable, and instead the two emulsions would migrate into one another. There exists a need in the art to be able to provide a multiple-phase product made with two distinct emulsions where the product is both visually and physically stable. Advantageously, the visually and physically stable compositions of the present invention comprising two or more discrete emulsions make it possible to incorporate into the composition otherwise incompatible ingredients, each providing a benefit to the end user.

SUMMARY

In view of the above-mentioned disadvantages of the gel-based products and methods, it is an object of the present disclosure to provide a composition having two or more discrete emulsions, in which the emulsions are in physical contact with each other and are each independently both physically and visually stable within the composition at ambient as well as other temperatures.

It is a further object of the present disclosure to provide a composition having two or more discrete emulsions, in which the emulsions are in physical contact with each other and are each independently both physically and visually stable within the composition at relatively low and relatively high temperatures encountered in the transportation and warehousing of such compositions.

It is a further object to provide a method of making a multiple-phase emulsion composition having a first and second emulsion, in which both emulsions are in physical contact with each other and are independently both physically and visually stable within the composition at ambient as well as other temperatures.

These and other objects and advantages of the composition and method of the present disclosure will be elaborated from the following detailed description.

DETAILED DESCRIPTION

It has been surprisingly discovered that two or more discrete emulsions can be in physical contact with each other, yet remain both physically and visually stable at ambient, as well as exhibit stability at temperatures typically encountered during transportation and warehousing of such products, for example, but not limited to, at temperatures as low as −4° F. and at temperatures as high as 150° F. It has also been found that two or more discrete emulsions can be in physical contact with each other and exhibit suitable freeze-thaw stability through at least one freeze-thaw cycle, preferably through at least three freeze-thaw cycles, and more preferably through at least five freeze-thaw cycles. Specifically, the emulsions remain visually distinct and the product retains its visual characteristics. Furthermore, each emulsion remains physically distinct, that is the two emulsions do not coalesce or migrate into one another and become a single emulsion. Each emulsion also remains chemically distinct, that is components of each emulsion do not migrate to the other.

Accordingly, in one embodiment, a composition is provided having a first emulsion and a second emulsion, where the emulsions are in physical contact with each other and are both visually and physically stable at ambient as well as other temperatures. In related embodiments, the compositions have more than two discrete emulsions in physical contact with each other, where the emulsions are both visually and physically stable at ambient as well as other temperatures. The two or more emulsions may be situated within a container.

The two or more discrete emulsions can be present in the compositions in any ratio. In one embodiment, there are two discrete emulsions present at 6% and 94% of the total composition. In another embodiment, there are two or more discrete emulsions each present in equivalent weight amounts. It will be readily understood to one of ordinary skill in the art that any ratio of the two or more discrete emulsions is contemplated within the scope of the present disclosure. All concentrations set forth herein are by weight percent of the total composition, unless otherwise stated.

Any type of emulsion well-known in the art can be used to arrive at a composition according to the present disclosure. Examples of suitable emulsion types include, but are not limited to, water-in-oil emulsions, oil-in-water emulsions, oil-in-oil emulsions, polyol-in-oil emulsions, water-in-silicone emulsions, silicone-in-water emulsions, and polyol-in-silicone emulsions.

In various embodiments, the two or more discrete emulsions are similar. In an embodiment, the emulsions are similar types of emulsions. In one embodiment, the two or more emulsions are similar with respect to their continuous phases. In another embodiment, the two or more emulsions are similar with respect to their discontinuous phases. In yet another embodiment, the two or more emulsions are similar with respect to both their continuous phases and their discontinuous phases. For example, in an embodiment with only two emulsions, if a first emulsion is an oil-in-water emulsion, a second emulsion that is similar would also be an oil-in-water emulsion. In a particular embodiment, the two or more discrete emulsions are each water-in-silicone emulsions. In still another embodiment, the two or more emulsions are similar with respect to the polarity of their continuous phases, discontinuous phases, or both. In still another embodiment, the two or more emulsions are similar with respect to the osmolarity of their continuous phases, discontinuous phases, or both. In various embodiments, the two or more emulsions are similar with respect to one or more of: emulsion type, continuous phase, discontinuous phase, polarity, and osmolarity.

In some embodiments, the two or more emulsions may be clear and transparent, translucent, or opaque, each of which can be colored or uncolored. In a particular embodiment with only two emulsions, the first emulsion is clear and transparent, and the second emulsion, suspended within the first emulsion, is colored, transparent, and/or opaque. To obtain a clear and transparent emulsion in accordance with the present disclosure, the refractive indices of the two phases within the emulsion must be matched to within about 0.0078 units of each other, or to within about 0.0041 units of each other, or to within about 0.0004 units of each other, or to within 0.0002 units of each other. To obtain an opaque emulsion, the refractive indices of the two phases within the emulsion are unmatched or an opacifying agent is added.

In accordance with this disclosure, "visually stable" is intended to refer to the composition maintaining its visual appearance at room temperature after being exposed to time and/or accelerated temperature conditions. For example, in a particular embodiment with only two emulsions, the first emulsion may be a clear emulsion and the second emulsion may be a colored opaque, colorless opaque, or a colored translucent emulsion, where the second emulsion is suspended within the first emulsion to create a visual pattern, such as a spiral or any other desired pattern. In this and related embodiments, "visually stable" refers both to the overall composition maintaining its visual pattern (e.g., no disruption of the original design, no muting of the visual design due to diffusion of one emulsion into the other, no distortion of the surface texture of the visual), as well as to each of the emulsions maintaining their individual appearance (e.g., the clear emulsion remains clear and not cloudy, and the colored emulsion retains its color).

In accordance with this disclosure, "physically stable" is intended to refer to each emulsion within the composition maintaining its individual emulsion characteristics. That is, the components of each emulsion do not diffuse into one another. Furthermore, the emulsions remain separate and physically distinct, and do not form a multiple emulsion.

In accordance with this disclosure, "chemically stable" is intended to refer to the ability to maintain the basic chemical properties of the components of the emulsion. For example, a chemically stable active ingredient would not degrade over time.

Visual, physical, or chemical stability can be measured by any appropriate analytical technique well known in the art. Such techniques include, but are not limited to, organoleptic analyses, pH measurement, viscosity measurement, Fourier Transform Infrared Spectroscopy, or mass spectroscopy. Stability can be measured under normal conditions at ambient temperature, or, in the alternative, can be approximated under accelerated conditions at higher temperatures.

The compositions according to the present disclosure also exhibit visual stability post freeze-thaw. Specifically, when subject to freezing and thawing, the compositions of the present disclosure maintain their visual appearance. By contrast, known gel systems exhibit a disrupted visual appearance when subject to alternating freezing/thawing, for instance, by the formation of ice crystals during freezing. Ice crystals permanently disrupt the visual effect, even after thawing.

In various embodiments, the compositions having two or more discrete emulsions are visually stable, physically stable, and/or chemically stable when evaluated at room temperature after being exposed to ambient temperature and freeze-thaw conditions. In various embodiments, the emulsions are stable at ambient temperature for at least three months, in particular for at least six months, preferably for at least one year, more preferably for at least two years, and most preferably for at least three years.

The emulsions of the present disclosure can include a variety of common ingredients and/or actives well known in the art. These include, but are not limited to, anaesthetics, anti-allergenics, antifungals, antimicrobials, anti-inflammatories, antiseptics, chelating agents, colorants, depigmenting agents, emollients, chemical exfoliants, mechanical exfoliants, film formers, fragrances, humectants, insect repellants, lubricants, moisturizers, pharmaceutical agents, preservatives, skin protectants, skin penetration enhancers, stabilizers, surfactants, thickeners, viscosity modifiers, vitamins, botanicals, solvents, pH modifiers, optical diffusers, sunscreens, biological actives, rheology modifiers, sensates, sensorial modifiers and mixtures thereof. The ingredients and/or actives can be neutral, acidic, basic, salt-forming, etc. The exact amounts will be determined by the skilled artisans, in light of factors related to the application. Amounts are adjusted to provide sufficient levels of the ingredients and/or actives to maintain the desired effect.

In various embodiments, the first emulsion can include an ingredient that would not otherwise be compatible with an ingredient contained in the second emulsion. The incompatibility of the ingredients can be due to a variety of reasons, including, but not limited to, pH stability, solubility, and reactivity. For example, a low pH ingredient can be included in the first emulsion, and a neutral pH ingredient can be included in the second emulsion.

In other embodiments, the inner phase of the first emulsion includes from about 25 to about 35% water, from about 25 to about 40% humectant, from about 0.01 to about 10% skin functioning/anti-aging ingredients such as alpha-hydroxy acids and/or water-soluble skin lighteners, from about 0.001 to about 2.0% colorants, and about 0.1 to about 5.0% mica, and the outer phase of first emulsion comprises from about 1 to about 3% UV-absorbers, from about 10 to about 30% silicones, and one or more silicone emulsifiers. In related embodiments, the humectant is glycerin.

In yet other embodiments, the inner phase of the second emulsion comprises from about 25 to about 35% water, from about 25 to about 40% humectant, and from about 0.01 to about 10% skin functioning/anti-aging ingredients such as alpha-hydroxy acids and/or water-soluble skin lighteners, and the outer phase of said second emulsion comprises from about 1 to about 3% UV-absorbers, from about 10 to about 30% silicones, and one or more silicone emulsifiers. In related embodiments, the humectant is glycerin.

In a particularly useful embodiment, alpha hydroxy acids are included in an emulsion in a composition according to the present disclosure. This embodiment is particularly advantageous over the prior art gel-based systems, wherein alpha hydroxy acids are incompatible with typical polyacrylate gel phases in a multi-phase composition.

In another embodiment, the two or more discrete emulsions have an aqueous phase, and the pH of the aqueous phase may be neutral, alkaline or acidic, depending on the requirements of the active ingredients present in the respective aqueous phases. Typically, the pH of an acidic aqueous phase will be from about 3 to below 7, preferably from about 3.7 to about 5.5. Such acidic aqueous phase can be used to contain, e.g., alpha hydroxy acids or other adjuvants that require an acidic environment for stability. Typically, the pH of an alkaline aqueous phase will be from above 7 to about 11, preferably from about 7.5 to about 8.5. Any combination thereof is suitable, e.g., both aqueous phases can be acidic, or both can be alkaline, or one acidic and one alkaline, or one neutral and the other either acidic or alkaline, or both neutral.

The emulsions for use in compositions according to the present disclosure can be prepared by any method known in the art. For example, in one embodiment, a water-in-silicone emulsion is prepared by combining and mixing the silicone ingredients until uniform, combining and mixing the water soluble ingredients until uniform, and then adding the water phase to the silicone phase using appropriate mixing conditions to achieve the desired viscosity. An example of appropriate mixing conditions would be to slowly add the water phase to the silicone phase under turbulent mixing conditions and to continue mixing until completely homogenous, then switch to homogenization using a rotor stator type homogenizer and mix until reaching the desired viscosity. When clear or transparent emulsions are required, the refractive index of each phase is measured, and the appropriate excipients are used to bring the refractive indices to within about 0.0078 units of each other, or to within about 0.0041 units of each other, or to within about 0.0004 units of each other, or to within 0.0002 units of each other. The formulator would select high refractive index materials to raise the overall refractive index of the respective phase and lower refractive index materials to decrease the refractive index of the respective phase. Examples of appropriate excipients include, but are not limited to, water and glycerin.

The compositions according to the present disclosure can be prepared by introducing the two or more discrete emulsions into a container by any method that achieves the desired visual effect. Each of the two or more discrete emulsions can be introduced into a container simultaneously, or in separate filling steps. Visual effects within the scope of the present disclosure include, but are not limited to, striped, marbled, rectilinear, interrupted striped, checkered, speckled, geometric, spotted, ribboned, helical, swirl, textured, grooved, ridged, waved, sinusoidal, spiral, laced, weaved, spotted, beads in predetermined arrangement, and tessellated. In a particular embodiment, a spiral visual effect is achieved using an apparatus and filling method such as that described in U.S. Pat. No. 6,516,838 to Thibiant et al., herein incorporated by reference in its entirety. In other embodiments, liquid filling machines made by Cozzolli Machine Company (Somerset, N.J.) or by Biosamia, SRL of Spello PG, Italy are used to introduce the two or more discrete emulsions to each other.

Various emulsions contemplated for use within the compositions disclosed herein as well as ingredients, adjuvants, excipients, and additives includable within the emulsions, as well as alternate methods of preparing the emulsions, can be found in the *Handbook of Cosmetic Science and Technology*, Eds. Barel et al. (2001), herein incorporated by reference in its entirety. Other non-limiting examples of ingredients, adjuvants, and excipients for use in cosmetic compositions are identified in *International Cosmetic Ingredient Dictionary and Handbook*, vol. 3, Section 3: Functions, p. 2747-2888 (11th Edition, 2006), herein incorporated by reference in its entirety.

Without being limited by theory in any way, it is believed the compositions and emulsions of the present disclosure are visually and physically stable because of a pseudo-equilibrium effect, whereby the two or more emulsions (i.e., the respective external phases) are sufficiently similar such that at the interface there is no force driving diffusion of ingredients from one emulsion to another. By contrast, in a composition having two or more emulsions mixed together not within the scope of the present disclosure, the composition will be driven towards equilibrium and ingredients within each emulsion will diffuse into one another.

In another embodiment, a method for making a cosmetic composition comprising two or more discrete emulsions in physical contact with each other where the two or more emulsions are both physically and visually stable within the composition at ambient or other temperatures is provided. The method according to this embodiment includes the steps of selecting a first emulsion and a second emulsion, and optionally one or more additional emulsions, such that the emulsions are similar, and introducing the selected emulsions into a container.

In related embodiments, the emulsions are selected from any well-known emulsions, including, but not limited to, water-in-oil emulsions, oil-in-water emulsions, oil-in-oil emulsions, polyol-in-oil emulsions, water-in-silicone emulsions, a silicone-in-water emulsions, and polyol-in-silicone emulsions.

In the methods of the present disclosure, the products are visually stable, physically stable, and/or chemically stable, both at ambient temperature and through freeze-thaw conditions. The products are stable at ambient temperature for at least six months, preferably for at least one year, more preferably for at least two years, and most preferably for at least three years. Real time stability is typically determined in the cosmetic arts by conducting accelerated stability testing on the product composition for one, two or three months at elevated temperatures.

In another embodiment, the method further includes the step of including within the emulsions any of a variety of common ingredients, adjuvants, excipients, and/or actives well known in the art. These include, but are not limited to, anaesthetics, anti-allergenics, antifungals, antimicrobials, anti-inflammatories, antiseptics, chelating agents, colorants, depigmenting agents, emollients, chemical exfoliants, mechanical exfoliants, film formers, fragrances, humectants, insect repellants, lubricants, moisturizers, pharmaceutical agents, preservatives, skin protectants, skin penetration enhancers, stabilizers, surfactants, thickeners, viscosity modifiers, vitamins, botanicals, solvents, pH modifiers, optical diffusers, sunscreens, biological actives, rheology modifiers, sensates, sensorial modifiers and mixtures thereof. The ingredients and/or actives can be neutral, acidic, basic, salt-forming, etc. The exact amounts will be determined by the skilled artisans, in light of factors related to the application. Amounts are adjusted to provide sufficient levels of the ingredients and/or actives to maintain the desired effect.

The compositions and methods of making same of the present disclosure are useful for a variety of cosmetic applications, including, but not limited to foundations, moisturizers, creams, sunscreens, surfactant/cleansing systems, oral care products, OTC drugs, artificial tanning, beach/suncare, footcare, patches, wipes, aqueous products, anhydrous products, spray products, ap/deo products, fragranced products, analgesics, insect repellents, cosmetic sticks, hair care products, conditioners, shampoos, hair colors, styling aids, decorative cosmetics including make-ups, nail polish, pressed powders, mascara, eyeliners, tattoos/body art, lipsticks, and concentrates thereof.

What follows are several non-limiting examples illustrating several particular embodiments, and are not included for the purpose of limiting the invention.

EXAMPLE 1

A low pH colored water-in-silicone emulsion suspended within a low pH clear water-in-silicone emulsion is prepared from two emulsions having the following compositions:

TABLE 1

| colored water-in-silicone emulsion | |
|---|---|
| Silicone phase | |
| Cyclopentasiloxane | 20% |
| Silicone elastomer | 5% |
| Dimethicone | 1% |
| Dimethicone copolyol | 1% |
| Water phase | |
| Water | 25-35% |
| Glycerin | 25-35% |
| Organic acid | 6% |
| Neutralizing base | adjust pH = 3.5-4.0 |
| Preservative | as needed |
| Hydrophilic colorants | as desired |

TABLE 2

| clear water-in-silicone emulsion | |
|---|---|
| Silicone phase | |
| Cyclopentasiloxane | 20% |
| Silicone elastomer | 5% |
| Dimethicone | 1% |
| Dimethicone copolyol | 1% |
| Fragrance | as desired |
| Water phase | |
| Water | 25-35% |
| Glycerin | 25-35% |
| Organic acid | 6% |
| Neutralizing base | adjust pH = 3.5-4.0 |
| Preservative | as needed |
| Hydrophilic colorants | as desired |

The refractive indices of the two phases of the clear water-in-silicone emulsion are matched to the other by using water and/or glycerin to bring the refractive indices to within 0.0004 units of each other.

Six parts by weight of the emulsion of Table 1 and 94 parts by weight of the emulsion of Table 2 are introduced into a suitable container using the apparatus set forth in U.S. Pat. No. 6,516,838 to Thibiant et al. to obtain the product composition.

EXAMPLE 2

A neutral pH colored water-in-silicone emulsion suspended within a low pH clear water-in-silicone emulsion is prepared from two emulsions having the following compositions:

TABLE 3

| colored water-in-silicone emulsion | |
|---|---|
| Silicone phase | |
| Cyclopentasiloxane | 20% |
| Silicone elastomer | 5% |
| Dimethicone | 1% |
| Dimethicone copolyol | 1% |
| Water phase | |
| Water | 25-35% |
| Glycerin | 25-35% |
| Preservative | as needed |
| Hydrophilic colorants | as desired |

TABLE 4

| clear water-in-silicone emulsion | |
|---|---|
| Silicone phase | |
| Cyclopentasiloxane | 20% |
| Silicone elastomer | 5% |
| Dimethicone | 1% |
| Dimethicone copolyol | 1% |
| Fragrance | as desired |
| Water phase | |
| Water | 25-35% |
| Glycerin | 25-35% |
| Organic acid | 6% |
| Neutralizing base | adjust pH = 3.5-4.0 |
| Preservative | as needed |
| Hydrophilic colorants | as desired |

The refractive indices of the two phases of the clear water-in-silicone emulsion are matched to the other by using water and/or glycerin to bring the refractive indices to within 0.0004 units of each other.

Six parts by weight of the emulsion of Table 3 and 94 parts by weight of the emulsion of Table 4 are introduced into a suitable container using the apparatus set forth in U.S. Pat. No. 6,516,838 to Thibiant et al. to obtain the product composition.

All publications and patents mentioned in the above specification are herein incorporated by reference. Various modifications and variations of the described method and system of the disclosure will be apparent to those skilled in the art without departing from the scope and spirit of the disclosure. Although the disclosure has been described in connection with specific embodiments, it should be understood that the disclosure as claimed should not be unduly limited to such specific embodiments. Indeed, various modifications of the described modes for carrying out the disclosed which are obvious to those skilled in the cosmetic arts or related fields are intended to be within the scope of the following claims.

What is claimed is:

1. A cosmetic composition comprising two or more emulsions, including a first emulsion and a second emulsion and optionally one or more additional emulsions, each of said two or more emulsions is discrete and comprising an inner phase and an outer phase, each of said two or more emulsions is independently selected from the group consisting of a water-in-silicone emulsion, and a polyol-in-silicone emulsion, each of said two or more emulsions is in physical contact with at least one other emulsion, and at least one of said two or more emulsions is visually distinct from the others, and each of said two or more emulsions is both physically and visually stable within the composition for at least six months at room temperature, and said composition is visually stable for at least six months at room temperature.

2. The composition according to claim 1, wherein each of said emulsions is a water-in-silicone emulsion.

3. The composition according to claim 1, wherein each of said emulsions is both physically and visually stable within the composition for at least one year at room temperature, and said composition is visually stable for at least one year at room temperature.

4. The composition according to claim 1, wherein each of said emulsions as well as said composition exhibit freeze-thaw stability through at least three freeze-thaw cycles.

5. The composition according to claim 1, wherein the inner phase of said first emulsion comprises from about 25 to 35% by weight water, from about 25 to about 40% by weight humectant, from about 0.01 to about 10% by weight skin functioning/anti-aging ingredients, from about 0.001 to about 2.0% by weight colorants, and about 0.1 to about 5.0% by weight mica.

6. The composition according to claim 1, wherein the outer phase of said first emulsion comprises from about 1 to 3% UV-absorbers, from about 10 to about 30% by weight silicones, and one or more silicone emulsifiers.

7. The composition according to claim 1, wherein the inner phase of said second emulsion comprises from about 25 to about 35% by weight water, from about 25 to about 40% by weight humectant, and from about 0.01 to about 10% by weight skin functioning/anti-aging ingredients.

8. The composition according to claim 1, wherein the outer phase of said second emulsion comprises from about 1 to about 3% by weight UV-absorbers, from about 10 to about 30% by weight silicones, and one or more silicone emulsifiers.

9. The composition according to claim 1, wherein refractive indices of both the inner and outer phases of said second emulsion, and optionally those of said one or more additional emulsions, are matched to within 0.0004 units, such that said second emulsion, and optionally said one or more additional emulsions, is transparent and/or iridescent, and such that said first emulsion is visible therethrough.

10. The composition according to claim 5, wherein the humectant is glycerin.

11. The composition according to claim 1, wherein each of said emulsions comprises an aqueous phase, wherein the pH of each of said aqueous phases is independently neutral, alkaline, or acidic.

12. A method for making a cosmetic composition comprising two or more discrete emulsions in physical contact with each other wherein the two or more emulsions as well as said composition are both physically and visually stable within the composition for at least six months at room temperature, the method comprising:
   a) selecting a first emulsion and a second emulsion and optionally one or more additional emulsions, such that said emulsions are similar; and
   b) introducing said selected emulsions into a container; wherein said emulsions are selected from the group consisting of a water-in-silicone emulsion, and a polyol-in-silicone emulsion.

13. The method according to claim 12, wherein said two or more emulsions as well as said composition are both physically and visually stable within the composition for at least one year at room temperature.

14. A cosmetic composition comprising at least two discrete polyol-in-silicone emulsions, each in physical contact with at least one other emulsion, at least one of said emulsions being visually distinct from any other emulsion, wherein each of said emulsions, as well as said composition, is independently both physically and visually stable within the composition for at least six months at room temperature, and wherein each of said emulsions as well as said composition exhibits freeze-thaw stability through at least one freeze-thaw cycle.

15. The composition according to claim 14 wherein a first emulsion is a clear emulsion and a second emulsion is a colored opaque, colorless opaque, or a colored translucent emulsion, wherein the second emulsion is suspended within the first emulsion to create a visual pattern.

16. The composition according to claim 15 wherein the pattern is one of striped, marbled, rectilinear, interrupted striped, checkered, speckled, geometric, spotted, ribboned, helical, swirl, textured, grooved, ridged, waved, sinusoidal, spiral, laced, weaved, spotted, beads in predetermined arrangement or tessellated.

17. The composition according to claim 16 wherein the pattern is a spiral.

18. The composition according to claim 15 wherein the pH of the first emulsion is in the range of about 3.5 to about 4.

19. The composition according to claim 1 wherein the first emulsion is a clear emulsion and the second emulsion is a colored opaque, colorless opaque, or a colored translucent emulsion, wherein the second emulsion is suspended within the first emulsion to create a visual pattern.

20. The composition according to claim 19 wherein the pattern is one of striped, marbled, rectilinear, interrupted striped, checkered, speckled, geometric, spotted, ribboned, helical, swirl, textured, grooved, ridged, waved, sinusoidal, spiral, laced, weaved, spotted, beads in predetermined arrangement or tessellated.

21. The composition according to claim 20 wherein the pattern is a spiral.

22. The composition according to claim 1 wherein the pH of the first and/or second emulsion is in the range of about 3.5 to about 4.

* * * * *